United States Patent
Zhang et al.

(10) Patent No.: US 8,200,308 B2
(45) Date of Patent: Jun. 12, 2012

(54) CONTINUOUS MEASUREMENT AND MAPPING OF PHYSIOLOGICAL DATA

(75) Inventors: Hongxuan Zhang, Schaumburg, IL (US); Detlef W. Koertge, Carpentersville, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 810 days.

(21) Appl. No.: 12/171,421

(22) Filed: Jul. 11, 2008

(65) Prior Publication Data

US 2009/0024016 A1    Jan. 22, 2009

Related U.S. Application Data

(60) Provisional application No. 60/950,420, filed on Jul. 18, 2007.

(51) Int. Cl.
*A61B 5/0215* (2006.01)
*A61B 5/01* (2006.01)
*A61B 5/042* (2006.01)

(52) U.S. Cl. ......... 600/374; 600/393; 600/549; 600/486

(58) Field of Classification Search .......... 600/372–374, 600/381, 393, 481, 486, 549; 374/137, 152, 374/166

See application file for complete search history.

(56) References Cited

U.S. PATENT DOCUMENTS

| | | | | |
|---|---|---|---|---|
| 4,776,340 A * | 10/1988 | Moran et al. | .................. | 600/327 |
| 5,275,162 A * | 1/1994 | Edwards et al. | ............. | 600/374 |
| 5,383,468 A * | 1/1995 | Nakayama et al. | ........... | 600/526 |
| 5,713,942 A * | 2/1998 | Stern et al. | ...................... | 607/98 |
| 5,868,743 A | 2/1999 | Saul et al. | ........................ | 606/49 |
| 5,924,997 A * | 7/1999 | Campbell | ...................... | 600/549 |
| 6,162,184 A | 12/2000 | Swanson et al. | ............. | 600/549 |
| 6,456,863 B1 | 9/2002 | Levin et al. | ................... | 600/374 |
| 6,607,517 B1 | 8/2003 | Dae et al. | ...................... | 604/500 |
| 6,908,434 B1 | 6/2005 | Jenkins et al. | ............... | 600/466 |
| 6,926,675 B2 | 8/2005 | Muuranto et al. | ............ | 600/526 |
| 7,153,649 B2 | 12/2006 | Smith et al. | ....................... | 435/2 |
| 7,206,637 B2 | 4/2007 | Salo | ................................ | 607/17 |
| 2003/0028114 A1* | 2/2003 | Casscells et al. | ............. | 600/474 |
| 2005/0124899 A1* | 6/2005 | Byrd et al. | .................... | 600/467 |

OTHER PUBLICATIONS

D. Tzivoni, A. Cribier, K. Kanmatsuse, C. Chew and W. Ganz, "Evaluation of changes in epicardial blood flow in experimental animals by cardiothermography", European Heart Journal, 1982, vol. 3, No. 3, No. 4, pp. 382-388.

* cited by examiner

*Primary Examiner* — Lee S Cohen
*Assistant Examiner* — Erin M Cardinal
(74) *Attorney, Agent, or Firm* — Alexander J Burke

(57) ABSTRACT

A catheter has a plurality of sensors and electrodes, wherein the sensors are arranged alternately and spaced apart from each other. A system for continuous measurement and mapping of physiological data may use such a catheter with a coupling unit for insulated coupling of the plurality of sensors with a measurement unit and a mapping unit for mapping values received from the sensors to a predefined matrix.

24 Claims, 5 Drawing Sheets

CONTINUOUS MEASUREMENT AND MAPPING OF PHYSIOLOGICAL DATA

CROSS-REFERENCE TO RELATED APPLICATIONS

This application claims the benefit of U.S. Provisional Application No. 60/950,420 filed on Jul. 18, 2007, entitled "CONTINUOUS TEMPERATURE MEASUREMENT AND MAPPING FOR INTRA-CARDIAC MONITORING SYSTEM", which is incorporated herein in its entirety.

TECHNICAL FIELD

The technical field of the present application relates to continuous measurement and mapping of physiological data.

BACKGROUND

The temperature measurement of heart tissue can be essential for a patient's safety, especially during high energy stimulation and ablation procedures in a heart operation. Usually a single temperature sensor is used to measure the local heat status at the tip of a catheter during cardiac ablation. Furthermore, during other electrophysiological (such as high-current stimulation) and hemodynamic cases, there is no method available for continuous temperature measurement and mapping of the heart and circulation system which may result in an over heating risk of the myocardium tissue, even unnecessary burning and permanent tissue damage.

Current cardiac hemodynamic and electrophysiological (EP) function monitoring utilize different kinds of approaches for patient signal/data conversion and acquisition, such as EP catheter for heart electrophysiological activity, pressure catheter for blood flow rate and cardiac output (CO) measurement, etc. However, there exist not enough methods and strategies for intra-cardiac tissue and blood temperature measurement and monitoring, except for single one tip-temperature monitoring during the ablation procedure. Cardiac temperature monitoring can provide more heart safety information as well as function estimation/evaluation, which can not be achieved using current hemodynamic and electrophysiological methods, such as the tissue safety during high-energy stimulation and acute myocardial ischemia (AMI) estimation/evaluation.

SUMMARY

In summary, there are several shortcomings and possible improvements with current hemodynamic and electrophysiological function monitoring strategies: For example, although the calculation relations between blood flow and blood pressure have been constructed, the function relations between cardiac tissue, temperature and blood flow have not been reliably and accurately determined and setup, which limit the medical application of temperature based analysis and monitoring, e.g. the tissue function and cardiac circulation evaluation during high energy stimulation and Pecutaneous Transluminal Coronary Angioplasty (PTCA) procedure. Current temperature monitoring is limited to single local point monitoring, such as the catheter tip-temperature monitoring in the ablation procedure, which may not provide enough temperature evaluation of the whole chamber or heart. Thus, there exists a need to spatially construct the temperature. Current cardiac hemodynamic and electrophysiological function monitoring cannot provide a temperature based cardiac function and tissue evaluation and predication. Also, it is desirable to provide for continuous temperature based tissue and circulation monitoring and mapping which could provide a reliable approach for medical application evaluation, such as over-burning risk analysis for atrial fibrillation ablation, low temperature indication for AMI monitoring, estimation and predication of myocardial infarction. Continuous temperature analysis and EP monitoring have not been able to be combined and utilized together, which may limit the medical application since EP monitoring may not provide enough tissue function estimation and analysis. A close-loop function analysis/estimation and adaptive feedback control strategies have not been efficiently setup. For example, during high energy stimulation and ablation procedures, the frequency, power (current and voltage), speed, etc, have not been reliably controlled and optimized. Thus there exists a need for multi-position temperature monitoring and a temperature feedback close-loop control for such a procedure. According to various embodiments, a continuous multi-channel mapping strategy for function evaluation, cardiac tissue and circulation monitoring as well as safety information is proposed.

According to an embodiment a system for continuous measurement and mapping of physiological data may comprise a catheter comprising a plurality of spaced apart sensors; a coupling unit for insulated coupling of the plurality of sensors with a measurement unit: and a mapping unit for mapping values received from the sensors to a predefined matrix.

According to a further embodiment, the sensors may be temperature sensors. According to a further embodiment, the system may comprise a plurality of catheters each comprising a plurality of spaced apart sensors. According to a further embodiment, the catheter further may comprises a plurality of electrophysiological (EP) electrodes spaced apart from the temperature sensors. According to a further embodiment, temperature sensors and EP electrodes may be arranged alternately. According to a further embodiment, the temperature sensors may be thermistors and the coupling unit may comprise a first isolating transformer for transmitting a current to the plurality of temperature sensors. According to a further embodiment, the coupling unit may further comprise for each temperature sensor an associated voltage to frequency converter and at least one second isolating transformer coupled to the voltage frequency converter. According to a further embodiment, each voltage to frequency converter may have a predefined frequency range which is non-overlapping with another frequency converter and a single isolating transformer coupled with the voltage of frequency converters. According to a further embodiment, the temperature sensors can be thermistors. According to a further embodiment, temperature mapping unit can be operable to track a heart function, blood flow or any possible abnormal temperature locations.

According to a further embodiment, the sensors may be pressure sensors. According to another embodiment, a catheter may comprise a plurality of sensors and electrodes, wherein the sensors are arranged alternately and spaced apart from each other. According to a further embodiment, the sensors can be temperature sensors such as thermistors or may be pressure sensors. According to a further embodiment, the catheter may further comprise a coupling unit for insulated coupling of the plurality of the thermistors with a measurement unit. According to a further embodiment, the coupling unit may comprise a first isolating transformer for transmitting a current to the thermistors. According to a further embodiment, the coupling unit may further comprise for each temperature sensor an associated voltage to frequency converter and at least one second isolating transformer coupled to the voltage frequency converter. According to a further embodiment, each voltage to frequency converter may have a predefined frequency range which is non-overlapping with another frequency converter and a single isolating transformer coupled with the voltage of frequency converters.

According to another embodiment, a method for continuously measuring and mapping of physiological data, may comprise the steps of providing a catheter comprising a plurality of spaced apart sensors; providing a coupling unit for insulated coupling of the plurality of sensors with a measurement unit; and mapping values received from the sensors to a predefined matrix.

According to a further embodiment, the sensors can be thermistors. According to a further embodiment, the method may further comprise the step of providing a plurality of catheters each comprising a plurality of spaced apart sensors and wherein each catheter further comprises a plurality of electrophysiological (EP) electrodes spaced apart from the temperature sensors. According to a further embodiment, the method may further comprise the step of transmitting power through a first isolating transformer for transmitting a current to the thermistors. According to a further embodiment, the method may further comprise the steps of measuring a voltage for each thermistor, convening the voltage into a signal having a frequency dependent on the voltage, transmitting the signal through a second isolating transformer, and converting the transmitted signal into a voltage. According to a further embodiment, the method may further comprise the step of tracking a heart function, blood flow or any possible abnormal temperature locations.

Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any preceding claimed embodiment(s).

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain, by way of example, the principles of the invention.

DETAILED DESCRIPTION

To achieve better monitoring and diagnosis for the cardiac operation, according to various embodiments, a method for continuous temperature measurement and mapping is proposed which may include an isolated continuous cardiac temperature measuring method and/or a multi-channel temperature mapping and function scanning strategy for heart and circulation system.

According to various embodiments, more efficient methods and strategies for cardiac function, tissue and circulation system monitoring, analysis, mapping, and evaluation as well as cardiac procedure application safety to the heart can be provided, which utilize continuous cardiac temperature monitoring, function scanning and mapping. Concurrently, the temperature monitoring and mapping technologies may also provide cardiac pathology estimation and prediction which other hemodynamic and EP monitoring can not perceive, such as temperature and its variability indicating overburning, low blood flow (ischemic region) and abnormal cardiac activity along conducting pathway.

Thus, the above mentioned shortcomings can be overcome and therefore the performance of the medical patient monitoring and analysis system will be improved. In summary, the following advantages over the conventional hemodynamic and electrophysiological techniques can be achieved: A continuous high-accurate temperature method and strategy for signal conversion and data transmission with high-voltage isolation and low noise interference. An easy and reliable calculation strategy for temperature and its variability with the tissue pathology, blood flow rate, and even cardiac output. A versatile multi-channel temperature monitoring strategy for cardiac tissue mapping and scanning, function evaluation, for both local region and chamber analysis, such as pathology analysis and prediction. A combined lead system for integration of both electrophysiological catheter and temperature lead system. The EP activity and temperature performance of the heart can be utilized together for more accurate cardiac diagnosis. An automatic feedback control strategy based on temperature monitoring and analysis which can more efficiently and accurately manipulate the current, voltage, frequency, etc, for stimulator and ablator, even disconnect the risky application.

The following describes embodiments that pertain to the circuit design, development and strategies of a new catheter system of integrating multi-channel EP and temperature lead systems; a hardware system for supplying power, converting/transmitting temperature signal, providing an accurate and safe temperature measuring and monitoring system to the catheter in the cardiac operation; and a strategy of multi-channel temperature mapping and scanning for cardiac pathology analysis and prediction.

Figure 1:
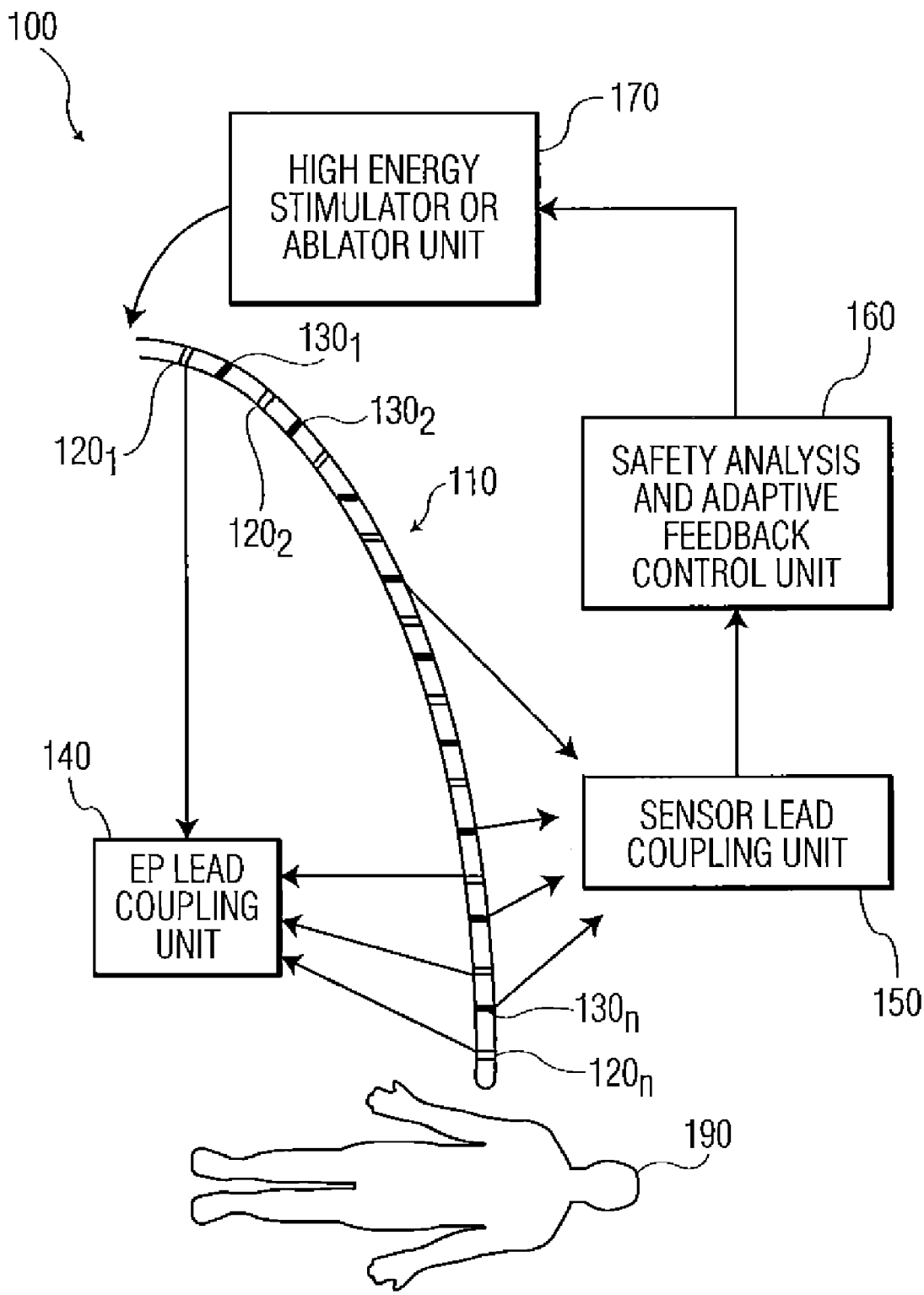
FIG. 1 shows an embodiment of a catheter having a plurality of temperature sensors and electrodes.

FIG. 1 shows an embodiment of a catheter 110 usable for a patient 190 having a non-conductive support structure that carries a plurality spaced apart EP electrodes or leads $120_1$, $120_2 \ldots 120_n$. In between the EP leads are arranged sensor leads $130_1$, $130_2 \ldots 130_n$ such as temperature sensors, pressure sensors or any other suitable sensor. According to an embodiment, thermistors can be preferably used as high precision temperature sensors as will be explained in more detail below. The EP leads are coupled to an EP lead coupling unit 140 for receiving signals suitable for stimulation or ablation provided by a high energy stimulator and/or ablator unit 170 whereas the sensor leads are coupled to a sensor measurement unit 150 such as a temperature measurement unit as will be explained in more detail below. To this end, the sensor unit 150 may be coupled with a safety analysis and adaptive feedback control unit 160 which can be coupled with the high energy stimulator and/or ablator unit 170. The high energy stimulator and/or ablator unit 170 sends output signals directly to the EP electrodes or via EP coupling unit 140.

According to one embodiment, one or more such multi-channel catheters 110 can be used in a Multi-channel close-loop automatic control for high energy stimulator and ablator system as shown in FIG. 1. Via the close loop feedback controlling based on temperature calculation and monitoring, the operation procedure, such as stimulation and ablation (energy, current, voltage, frequency, pulse duration, etc) can be optimally adjusted. In FIG. 1, according to one embodiment, the EP and temperature lead integration catheter 110 is employed to capture both cardiac electrophysiological activity and temperature (heat and energy) information, which can be used to construct a 2D or 3D EP function mapping as well as temperature mapping for pathology analysis and cardiac function image registration as will be explained in more detail below.

Figure 2:
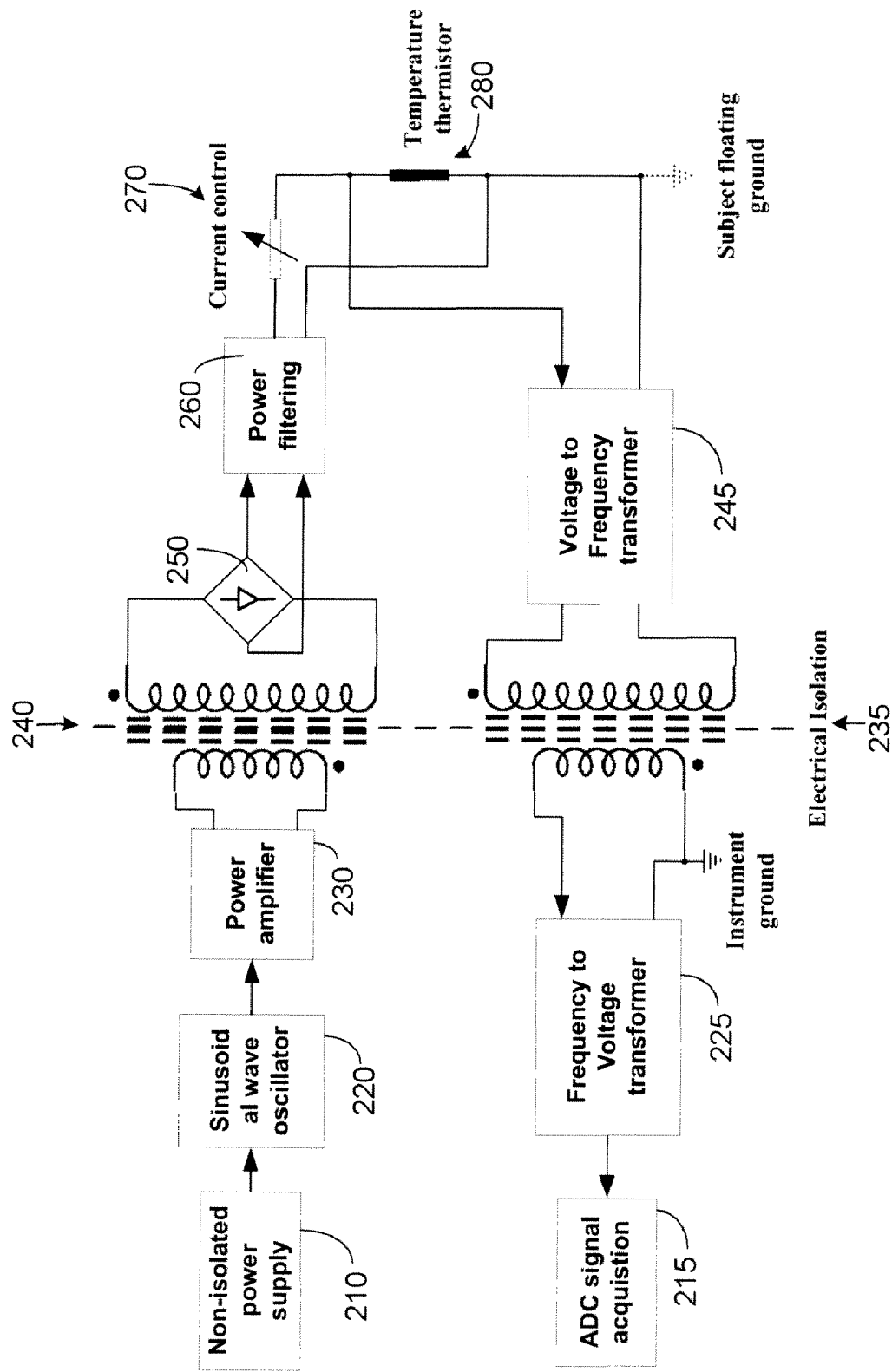
FIG. 2 shows a mapping scheme using data derived from one or more catheters according to an embodiment.

Patient safety requires high voltage isolation between the subject 190 and the instrument 100. According to an embodiment as shown in FIG. 2, a high voltage isolation transformer 240 is used to transmit the power to the isolated side (floating GND, patient ground) and supply the temperature measuring sensors. To this end, according to one embodiment a non-isolated power supply 210 is coupled with a sinusoidal wave oscillator 220 followed by a power amplifier 230 which feeds one side of transformer 240. Other circuits designs can be used to provide the appropriate power to the instrument side of transformer 240. The patient side of transformer 240 is coupled with a rectifier 250 which feeds a power filtering unit 260. The power filtering unit 260 is coupled with a current control unit 270 to control the current fed to a temperature thermistor 280. The temperature of the cardiac tissue and circulation can be captured by thermistor 280 and converted to frequency signals by a high accuracy voltage to frequency converter 245. The output of voltage to frequency converter 245 is coupled with the patient side of a second transformer 235. The instrument side of second transformer 235 is coupled with a frequency to voltage transformer 225 which outputs a voltage fed to an analog-to-digital converter unit 215.

The voltage to frequency converter 245 can provide very accurate temperature measurement and this make it reliable to analyze and evaluate the temperature change and its variability. The temperature signal is converted and coded into a frequency by voltage to frequency converter (VFC) and then the frequency signal after transformer 235 is decoded back to a temperature signal by a frequency to voltage converter (FVC). According to an embodiment, the VFC and FVC are used as a pair for a continuous high precision temperature signal transmission. FIG. 2 illustrates a single continuous temperature measuring strategy and related hardware. The isolated temperature measurement and transmission provide not only safety but low noise and low artifacts distortion since VFC and FVC can greatly reduce the unwanted noise by controlling the signal frequency bandwidth.

This measurement strategy is able to achieve continuous temperature monitoring with high accuracy which may provide a method for more stable and accurate measurement for any kind of minute changes of the myocardial tissue. For example, the local temperature drop or variation due to myocardial ischemia or infarction can be accurately and correctly captured by such an arrangement. Single local measurement can provide the temperature value as well as temperature variation with time, which may make it possible to predict the pathology of ROI (region of interest) of the heart that electrophysiological signal might not be able to catch and perceive, especially for high risky cardiac tissue point during high-energy stimulation and ablation.

Figure 3:
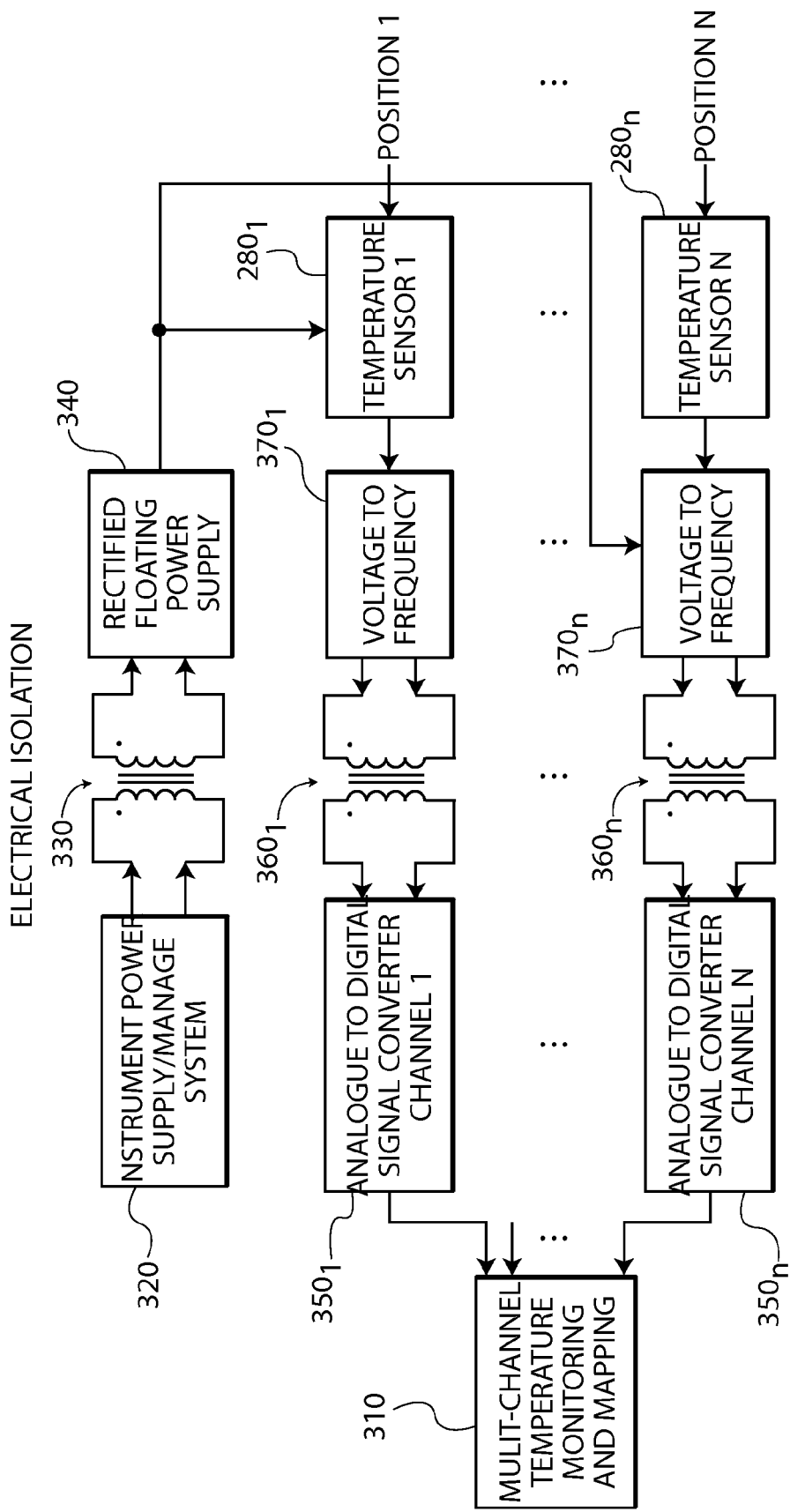
FIG. 3 shows an embodiment of a circuit usable for transmitting measurements from a catheter according to an embodiment.

Based on such a single channel temperature measuring strategy and concept, according to another embodiment a multi-channel channel temperature measuring and monitoring 300 can be provided as shown in FIG. 3. The multi-channel temperature sensors can be from one temperature catheter or a combination of several temperature lead systems. Via the multi-lead temperature reconstruction, the temperature mapping and intra-cardiac heat flow scanning image can be achieved as will be explained below in more detail, which may provide a new method for cardiac pathology analysis and prediction, such as myocardial ischemia, etc. FIG. 3 shows the schematic of multi-channel temperature monitoring and analysis system. According to an embodiment, a central instrument power supply/management unit 320 provides the appropriate power via a first transformer 330 to a rectifier floating power supply unit 340. This unit 340 may supply a plurality of temperature sensors $130_1 \ldots 130_n$. Each temperature sensor $280_1 \ldots 280_n$ sends its output signal to an associated voltage to frequency converter $370_1 \ldots 370_n$ which in turn transfers its output signal over an associated transformer $360_1 \ldots 360_n$ to an analog-to-digital signal converter (ADC) unit $350_1 \ldots 350_n$. The respective digital signals from ADC units $350_1 \ldots 350_n$ are fed to a multi channel temperature monitoring and mapping unit 310. According to another embodiment, a single ADC unit and respective multiplexer arrangement can be used to convert the temperature signals.

Figure 4:
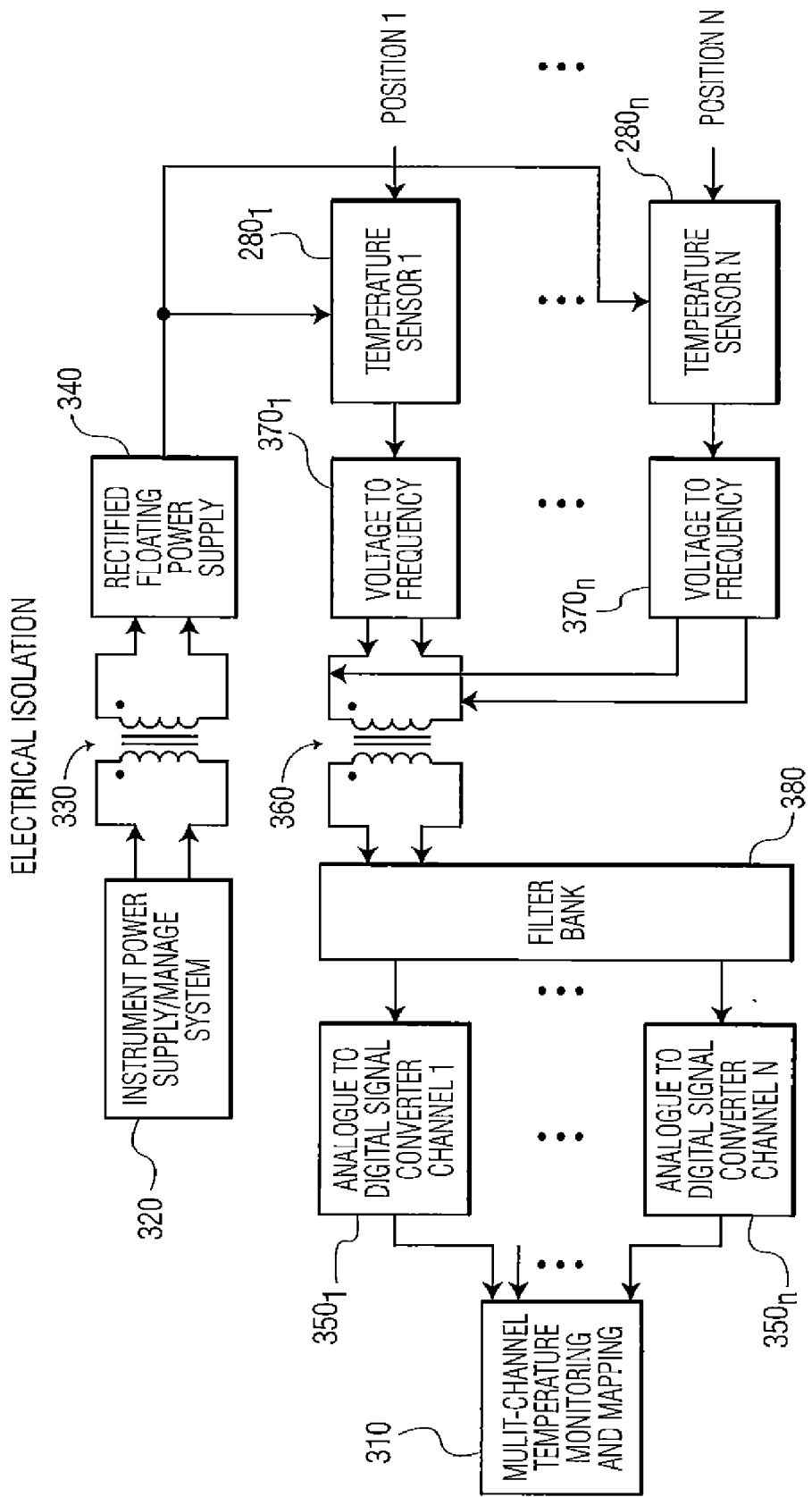
FIG. 4 shows an embodiment of a circuit usable for transmitting measurements from a catheter according to another embodiment.

Temperature sensors, such as thermistors $280_1 \ldots 280_n$ can monitor different positions or tissue of the cardiac system, such as RV, RA or different points of the same chamber. Using multi-channel temperature sensors, a user is able to track the temperature of multi heart tissue points of interest, especially monitoring the blood flow pathway of different chambers and tissue function of the cardiac excitation pathway. According to another embodiment, as shown in FIG. 4, multi-channel temperature signals can be transmitted by one isolated transformer 360 with different signal frequency bands. To this end, each voltage to frequency converter $370_1 \ldots 370_n$ may for example have a non-overlapping dedicated frequency range. On the instrument side an appropriate filter bank 380 may be provided to separate the signals from the various temperature sensors $280_1 \ldots 280_n$.

The multi-channel temperature monitoring system 310 includes multi-lead temperature catheter 110, continuous temperature signal conversion and acquisition, temperature component mapping algorithm, and evaluation strategy. FIG. 4 shows the schematic of multi lead based temperature matrix mapping system 310. By temperature scanning, tracking, and mapping, the function and abnormality of the whole, single chamber, and even blood flow pathway can be accurately captured. At the same time, the preferred embodiments of the current invention also include calculation strategy for relations between blood flow and temperature changes and variability, both for cardiac chamber, cardiac vessel, and heart CO. For example:

$$BF = f(t_1, \ldots, t_n, \Delta t_1, \ldots, \Delta t_n, \delta t_1, \ldots, \delta t_n, \ldots)$$

In which, BF stands for the blood flow amount or rate; $f(\bullet)$ is the linear or nonlinear function between blood flow index and temperature calculation; $t_i, \Delta t_i, \delta t_i, \ldots$ are temperature related calculation (temperature changes, standard deviation, etc.)

Via the calculation and modeling of the blood flow and temperature mapping, an estimation and evaluation of the cardiac function and health can be derived. For instance, BF calculation and pattern of every single heart beat can be achieved with continuous real time temperature mapping and the pattern changes/variability with time may be utilized for clinical analysis and diagnosis. BF can be used as a cardiac healthy and function index, even prediction of the pathology since temperature changes may be present much earlier than electrophysiological index in a lot of cases. By constructing the calculation between blood flow and temperature, a real time temperature and instant blood flow rate mapping can be achieved. Temperature based BF calculation may be used as healthy index clinically.

Figure 5:
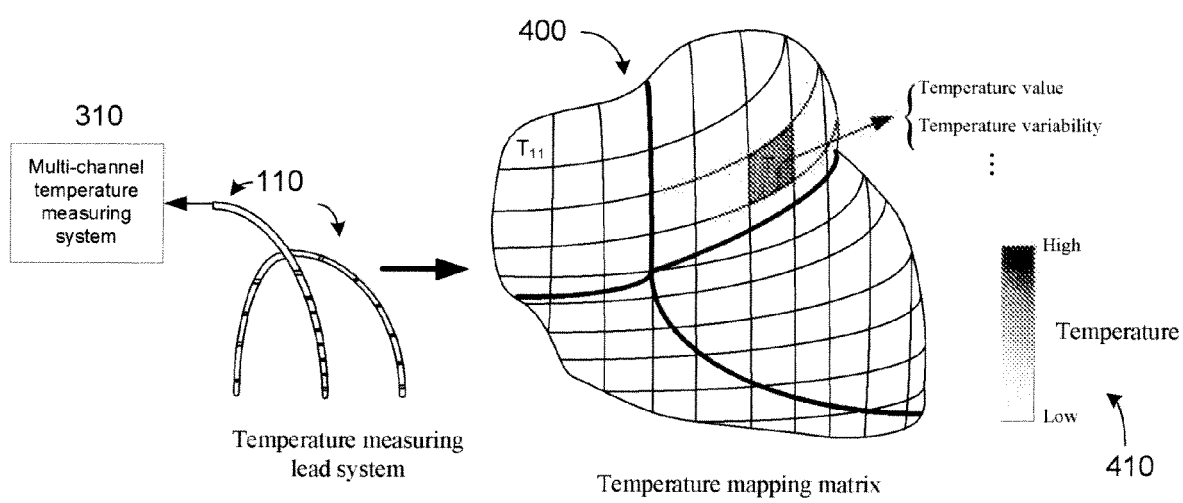
FIG. 5 shows another embodiment of a circuit usable for transmitting measurements from a catheter having multiple sensors according to an embodiment.

Placement of the catheters can be tracked according to known methods such as any kind of known medical imaging so that the measurement of the different temperatures by the sensors, as for example shown in FIG. 5, corresponds to the assumed matrix. Points of interest not covered by the catheter sensors can be obtained by interpolation.

In FIG. 5, the temperatures of heart tissue and vessels are measured by multi-leads using different temperature catheters 110. FIG. 5 shows in particular two catheters placed within a heart at predetermined positions. The derived temperature values can be constructed with an element matrix 400 for heart and blood temperature system. Every element $T_{ij}$ in the temperature mapping matrix 400 stands for the temperature value, variability, or other derived temperature index. With the temperature mapping, it is possible to track the heart function, blood flow, and any possible abnormal temperature locations which may indicate pathology, such as over burning by ablation/stimulation, ischemic/infracted myocardial points and low blood flow areas. According to an embodiment, as indicated by the shaded temperature scale 410 on the right, a color scheme can be used, wherein the color of the matrix component/unit stands for the high or low of the temperatures for the corresponding cardiac points $T_{ij}$. Other coding of the temperature may apply according to various embodiments.

As discussed above, according to an embodiment, the EP signal measurement and temperature measurement (or other hemodynamic measurement, such as blood pressure.) can be combined by integrating temperature thermistors (leads) $130_1 \ldots 130_n$ and electrophysiological signal leads $120_1 \ldots 120_n$ into one catheter 110 as shown in FIG. 1. The new catheter 110 can acquire the electrophysiological signals (ICEG, intra-cardiac electrograms) and temperature at the same time. The information combination and fusion of EP signal matrix and temperature (hemodynamic) matrix can provide more accurate and reliable signal measurement, function evaluation, and cardiac tissue/circulation monitoring as well as subject safety and operation procedure risk warning information. The close loop system for high energy stimulator and ablator controlling based on the multi temperature lead is illustrated in FIG. 1. Electrophysiological signal and hemodynamic signals usually come from different mechanism which may result in different kind of clinical symptom. For example, electrophysiological activity of the heart are acute index while hemodynamic are usually slower, such as long term low blood flowing in the coronary artery resulting in myocardial ischemia and slight ST segment changes of the EP signals. According to various embodiments, utilizing both EP signal as well as hemo signals, may provide more reliable diagnosis and then earlier treatment with less risk for subject.

The principles according to various embodiments can also be extended to other EP and hemodynamic measurement, such as blood pressure mapping system for heart, blood flow rate mapping for heart and vessels, etc. Optimistically, using the same application concept, the EP lead, hemodynamic lead and temperature lead systems can be integrated together, which can greatly reduce the time, complexity and patient safety risk for cardiac operation.

The invention, therefore, is well adapted to carry out the objects and attain the ends and advantages mentioned, as well as others inherent therein. While the invention has been described and is defined by reference to particular preferred embodiments of the invention, such references do not imply a limitation on the invention, and no such limitation is to be inferred. The invention is capable of considerable modification, alteration, and equivalents in form and function, as will occur to those ordinarily skilled in the pertinent arts. The described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A system for continuous measurement and mapping of physiological data comprising:
    an intra-cardiac catheter comprising a plurality of spaced apart temperature sensors for concurrently sensing a plurality of temperatures at different locations within a patient heart;
    a coupling unit configured for isolated coupling of data representing the sensed plurality of temperatures from the plurality of temperature sensors with a measurement unit; and
    a mapping unit, in said measurement unit, configured for mapping individual values received from said sensors to corresponding respective particular elements of a matrix of a plurality of elements associated with heart locations, individual elements of said plurality of elements comprising a temperature value and temperature variability data of a particular respective heart location enabling monitoring heart function, blood flow, and abnormal temperature locations indicating pathology.

2. The system according to claim 1, wherein said coupling unit provides isolated coupling of data representing the sensed plurality of temperatures of said plurality of temperature sensors using an isolation device and voltage to frequency converter using a predetermined frequency range.

3. The system according to claim 2, comprising a plurality of catheters each comprising a plurality of spaced apart sensors.

4. The system according to claim 2, wherein said catheter further comprises a plurality of electrophysiological (EP) electrodes spaced apart from said temperature sensors.

5. The system according to claim 3, wherein temperature sensors and EP electrodes are alternately positioned along at least a portion of the catheter catheters.

6. The system according to claim 2, wherein the temperature sensors are thermistors and said coupling unit comprises a first isolating transformer for transmitting a current to said plurality of temperature sensors and said coupling unit further comprises for each temperature sensor an associated voltage to frequency converter and individual voltage to frequency converters use non-overlapping frequency ranges.

7. The system according to claim 6, wherein said coupling unit comprises at least one second isolating transformer coupled to at least one of the voltage to frequency converters.

8. The system according to claim 2, wherein the temperature sensors are thermistors.

9. The system according to claim 2, wherein the mapping unit is operable to track a heart function, blood flow or abnormal temperature locations.

10. A system for continuous measurement and mapping of physiological data comprising:
    a catheter comprising a plurality of spaced apart thermistors;
    a coupling unit configured for isolated coupling of the plurality of thermistors with a measurement unit and including a first isolating transformer for transmitting a current to said plurality of thermistors and said coupling unit further comprises for each thermistor an associated voltage to frequency converter and at least one second isolating transformer coupled to said voltage to frequency converter and each voltage to frequency converter has a predefined frequency range which is non-overlapping with another frequency converter; and a mapping unit configured for mapping values received from said thermistors to a predefined matrix.

11. A system for continuous measurement and mapping of physiological data comprising:

an intra-cardiac catheter comprising a plurality of spaced apart pressure sensors for concurrently sensing a plurality of pressures at different locations within a patient heart;

a coupling unit configured for isolated coupling of data representing the sensed plurality of pressures from the plurality of pressure sensors with a measurement unit; and a mapping unit, in said measurement unit, configured for mapping individual values received from said sensors to corresponding respective particular elements of a matrix of a plurality of elements associated with heart locations, individual elements of said plurality of elements comprising a pressure value and pressure variability data of a particular respective heart location enabling monitoring heart function, blood flow, and abnormal pressure locations indicating pathology.

12. An intra-cardiac catheter system comprising a plurality of temperature sensors and electrodes, wherein the temperature sensors and electrodes are alternately positioned along at least a portion of a catheter and are spaced apart from each other, said temperature sensors concurrently sensing a plurality of temperatures at different locations within a patient heart; and a mapping unit configured for mapping individual values received from said sensors via a coupling unit, to corresponding respective particular elements of a matrix of a plurality of elements associated with heart locations, individual elements of said plurality of elements comprising a temperature value, electrode signal value and temperature variability data of a particular respective heart location enabling monitoring heart function, blood flow, and abnormal temperature locations indicating pathology.

13. The catheter system according to claim 12, wherein the coupling unit provides isolated coupling of data representing the sensed plurality of temperatures of said plurality of temperature sensors using an isolation device and voltage to frequency converter using a predetermined frequency range.

14. The catheter system according to claim 13, wherein the temperature sensors are thermistors.

15. The catheter system according to claim 14, wherein said coupling unit comprises a first isolating transformer for transmitting a current to said thermistors.

16. The catheter system according to claim 15, wherein said coupling unit further comprises for each temperature sensor an associated voltage to frequency converter and at least one second isolating transformer coupled to at least one of said voltage to frequency converters.

17. An intra-cardiac catheter system comprising a plurality of pressure sensors and electrodes, wherein the pressure sensors and electrodes are alternately positioned along at least a portion of a catheter and are spaced apart from each other, said pressure sensors concurrently sensing a plurality of pressures at different locations within a patient heart; and a mapping unit configured for mapping individual values received from said sensors via a coupling unit, to corresponding respective particular elements of a matrix of a plurality of elements associated with heart locations, individual elements of said plurality of elements comprising a pressure value, electrode signal value and pressure variability data of a particular respective heart location enabling monitoring heart function, blood flow, and abnormal pressure locations indicating pathology.

18. A catheter comprising a plurality of sensors and electrodes, including, a plurality of thermistors and electrodes alternately positioned along at least a portion of the catheter and spaced apart from each other;

a coupling unit configured for isolated coupling of said plurality of thermistors with a measurement unit using a first isolating transformer for transmitting a current to said thermistors and for each thermistor an associated voltage to frequency converter and each voltage to frequency converter has a predefined frequency range which is non-overlapping with another frequency converter and a single isolating transformer coupled with said voltage to frequency converters.

19. A method for continuously measuring and mapping of physiological data, comprising the steps of:

using an intra-cardiac catheter comprising a plurality of spaced apart temperature sensors for concurrently sensing a plurality of temperatures at different locations within a patient heart;

electrically coupling data representing the sensed plurality of temperatures from the plurality of temperature sensors to a measurement unit;

using said measurement unit for mapping individual values received from said sensors to corresponding respective particular elements of a matrix of a plurality of elements associated with heart locations, individual elements of said plurality of elements comprising a temperature value and temperature variability data of a particular respective heart location enabling monitoring heart function, blood flow, and abnormal temperature locations indicating pathology.

20. The method according to claim 19, wherein said sensors are thermistors and including the step of coupling of data representing the sensed plurality of temperatures of said plurality of temperature sensors using an isolation device and voltage to frequency converter using a predetermined frequency range.

21. The method according to claim 20, further comprising the step of transmitting power through a first isolating transformer for transmitting a current to said thermistors.

22. The method according to claim 21, further comprising the steps of measuring a voltage for each thermistor, converting said voltage into a signal having a frequency dependent on said voltage, transmitting said signal through a second isolating transformer, and converting said transmitted signal into a voltage.

23. The method according to claim 20, further comprising the step of tracking a heart function, blood flow or abnormal temperature locations.

24. The method according to claim 19, further comprising the step of providing a plurality of catheters each comprising a plurality of spaced apart temperature sensors and wherein each catheter further comprises a plurality of electrophysiological (EP) electrodes spaced apart from said temperature sensors.

* * * * *